(12) United States Patent
Gan

(10) Patent No.: US 7,674,600 B2
(45) Date of Patent: Mar. 9, 2010

(54) ASSAYS FOR MEASURING PHOSPHATE MODIFICATION ENZYME ACTIVITY

(75) Inventor: Qing-Fen Gan, Palo Alto, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 49 days.

(21) Appl. No.: 12/001,804

(22) Filed: Dec. 13, 2007

(65) Prior Publication Data

US 2008/0145880 A1 Jun. 19, 2008

Related U.S. Application Data

(60) Provisional application No. 60/875,268, filed on Dec. 15, 2006.

(51) Int. Cl.
 *C12Q 1/48* (2006.01)
(52) U.S. Cl. .......................... 435/15; 435/21
(58) Field of Classification Search ............... 435/15, 435/21
 See application file for complete search history.

(56) References Cited

U.S. PATENT DOCUMENTS 6,203,994 B1 * 3/2001 Epps et al. .................. 435/7.1
6,410,254 B1 * 6/2002 Finer et al. .................. 435/21
7,070,921 B2 * 7/2006 Huang et al. .................. 435/4
2002/0034766 A1 * 3/2002 Huang et al. ................. 435/7.1
2007/0037215 A1 * 2/2007 Patton ........................ 435/7.1
2007/0190588 A1 * 8/2007 Ornatsky ..................... 435/15

FOREIGN PATENT DOCUMENTS

WO WO 2006/106340 10/2006

OTHER PUBLICATIONS

Beasley, J. R., et. al. "Evaluation of compounds Interference in Immobilized Metal Ion Affinity-Based Fluorescence Polarization Detection with a Four Million Member Compound Collection," *Assay and Drug Development Technologies*, 2003, vol. 1 (3), pp. 455-459.
Rininsland, F. et. al., "Metal ion-mediated polymer superquenching for highly sensitive detection of kinase and phosphatase activities," *PNAS*, 2004, vol. 101 (43), pp. 15295-15300.
Zhou, H. et. al., "Zirconium Phosphonate-Modified Porous Silicon for Highly Specific Capture of Phosphopeptides and MALDI-TOF MS Analysis," *J. of Proteome Res.*, 2006, vol. 5 (9), pp. 2431-2437.

* cited by examiner

*Primary Examiner*—Ralph Gitomer
(74) *Attorney, Agent, or Firm*—David J. Chang

(57) ABSTRACT

The present invention relates to assays that can measure the activity of enzymes that catalyze phosphate modifications, such as kinases, phosphatases, cyclases and phosphodiesterases. The assays can also be used to identify and screen for substances that modulate the activity of kinases, phosphatases, cyclases and phosphodiesterases.

4 Claims, 2 Drawing Sheets

ASSAYS FOR MEASURING PHOSPHATE MODIFICATION ENZYME ACTIVITY

CROSS REFERENCE TO RELATED INVENTIONS

This application claims the benefit of priority of U.S. Provisional Patent Application Ser. No. 60/875,268 filed Dec. 15, 2006, which is incorporated herein by reference in its entirety.

FIELD OF THE INVENTION

This invention pertains to biological assays for enzymes that catalyze phosphate modifications.

BACKGROUND OF THE INVENTION

Protein phosphorylation and dephosphorylation are used by cells as a general signal transduction mechanism usually in response to external stimuli. The proteins that carry out these phosphate modifications are enzymes called kinases (phosphorylation) and phosphatases (dephosphorylation). Kinases and phosphatases can be classified into two families depending on the amino acid residue that is (de)phosphorylated: tyrosine kinases (phosphatases) and serine/threonine kinases (phosphatases). Other enzymes that are important in cellular signal transduction pathways include cyclases that can produce cyclic nucleotides such as cyclic AMP (cAMP) and cyclic GMP (cGMP) which are important second messengers, and phosphodiesterases that hydrolyse the cyclic nucleotides to form the corresponding noncyclized nucleotide monophosphates (i.e. AMP and GMP). Due to their important roles in regulating cell function, all these enzymes are important target molecules for the discovery and development of novel pharmaceutical therapeutics.

Traditional methods of measuring the state of phosphorylation of cellular proteins are based on incorporation of radioactive $^{32}$P-orthophosphate. The $^{32}$P-phosphorylated proteins are separated on a gel and subsequently visualized using a phospho-imager. Alternatively, phosphorylated tyrosine residues may be bound via binding of radiolabelled anti-phosphotyrosine antibodies and detected by immunoassays, for example immunoprecipitation or blotting. Since these methods need to detect radioisotopes, they are time-consuming and also, owing to the safety aspects involved in the handling of radioactive substances, not suitable for ultra high throughput screening (uHTS).

In more recent methods, the radioactive immunoassays are replaced with ELISAs (enzyme-linked immunosorbent assays). These methods use purified substrate proteins or synthetic peptide substrates which have been immobilized to a substrate surface. After a kinase action, the extent of phosphorylation is quantified by the binding of anti-phosphotyrosine antibodies coupled to an enhancer enzyme such as peroxidases, for example, to the phosphorylated immobilized substrates.

Epps. et al. (U.S. Pat. No. 6,203,994) describe a fluorescence-based HTS assay for protein kinases and phosphatases, which makes use of fluorescently labelled phosphorylated reporter molecules and antibodies which bind specifically to the phosphorylated reporter molecules. Binding is measured by means of fluorescence polarization, fluorescence quenching or fluorescence correlation spectroscopy (FCS). This method has the intrinsic disadvantage of only good generic antibodies (e.g. clone PT66, PY20, Sigma) being available for phosphotyrosine substrates. Only a few examples of suitable anti-phosphoserine or anti-threonine antibodies have been reported (e.g. Bader B. et al., Journal of Biomolecular Screening, 6, 255 (2001), Panvera kit no. P2886). These antibodies, however, have the property of recognizing not only phosphoserine but also the neighbouring amino acids as epitope. It is known, however, that kinases function very substrate-specifically and that substrate sequences can differ greatly. Therefore, anti-phosphoserine antibodies cannot be used as generic reagents.

Perkin Elmer (Wallac) provide an assay for tyrosine kinases, which is based on time-resolved fluorescence and an energy transfer from europium chelates to allophycocyanine (see also EP 929 810). Here too, the process is limited essentially to tyrosine kinases, due to the use of antibodies.

Recently, Molecular Devices (U.S. Pat. No. 7,070,921) have provided nanoparticles with charged gallium cations on the surface as a generic binding reagent suitable for phosphorylation reactions to measure kinase and phosphatase activities as well as for nucleotide cyclization and decyclization reactions to measure cyclase and phosphodiesterase activities.

SUMMARY OF THE INVENTION

The present invention describes assays for detecting the activity of enzymes that can catalyze phosphate modifications on their substrates, based on the ability of the metal ions indium (III) and zirconium (IV) to bind specifically to phosphorylated molecules. The assays can be used for enzymes such as kinases and phosphatases that phosphorylate or dephosphorylate polypeptide molecules and for enzymes such as cyclases and phosphodiesterases that cyclize or decyclize nucleotide molecules.

Accordingly, the present invention provides for a method for assaying the activity of an enzyme that can catalyze a phosphate modification on a substrate to form a product, said method comprising the steps of contacting the substrate with the enzyme in the presence of indium (III) ion or zirconium (IV) ion, wherein the indium (III) ion or zirconium (IV) ion can bind to either the substrate or the product but not to both; measuring the extent of binding between the indium (III) ion or ziroconium (IV) ion and the substrate or the product; and correlating the extent of binding with the activity of the enzyme; wherein the enzyme is selected from the group consisting of kinases, phosphatases, cyclases and phosphodiesterases.

The present invention also provides for a method of screening for a substance that modulates the activity of an enzyme that can catalyze a phosphate modification on a substrate to form a product, said method comprising the steps of contacting the substrate and enzyme in the presence or absence of the substance and in the presence of indium (III) ion or zirconium (IV) ion, wherein the indium (III) ion or zirconium (IV) ion can bind to either the substrate or the product but not to both; measuring the extent of binding between the indium (III) ion or ziroconium (IV) ion and the substrate or the product; and determining the ability of the substance to modulate the extent of binding which correlates with the activity of the enzyme; wherein the enzyme is selected from the group consisting of kinases, phosphatases, cyclases and phosphodiesterases.

The foregoing and other advantages and features of the invention, and the manner in which the same are accomplished, will become more readily apparent upon consideration of the following detailed description of the invention taken in conjunction with the accompanying examples, which illustrate exemplary embodiments.

DETAILED DESCRIPTION OF THE INVENTION

Definitions

Figure 1:
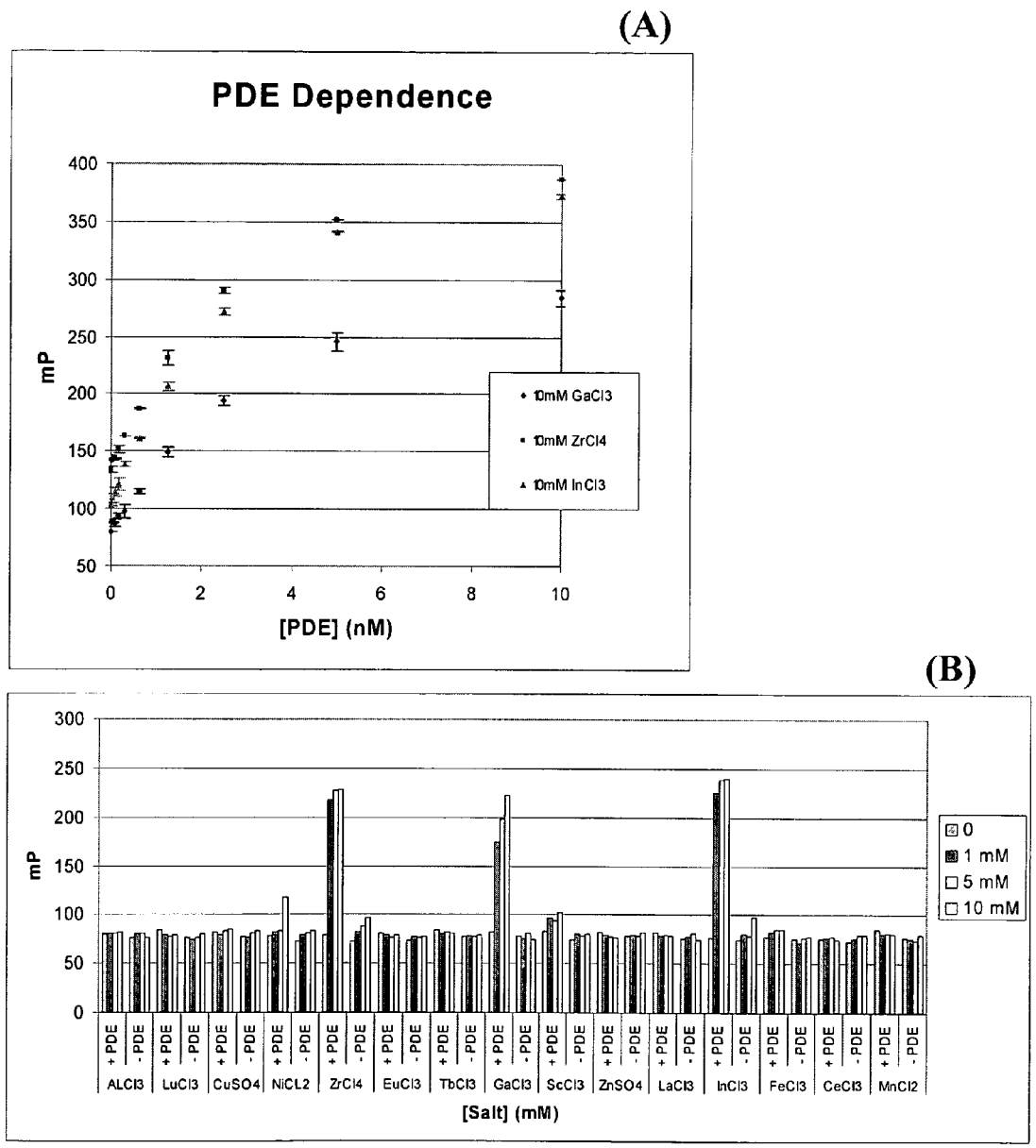
FIG. 1 shows the results of a phosphodiesterase assay using fluorescence polarization as the detection measurement. (A) The assay was run using various concentrations of phosphodiesterase or (B) various metal ions.

The term "phosphate modification" refers to the introduction (phosphorylation) or removal (dephosphorylation) of a phosphate group to or from an organic molecule such as a polypeptide or to the formation (cyclization) or degradation (decyclization) of a ring connecting a phosphate group and a nucleoside in a nucleotide. A common cyclization forms cAMP and cGMP from ATP and GTP, respectively, by removing two phosphate groups from the nucleotide triphosphates and joing the free end of the remaining phosphate group to the sugar in the remaining nucleotide monophsophate. A common decyclization reaction degrades the ring to form noncyclized AMP and noncyclized GMP from cAMP and cGMP, respectively.

The term "substrate" refers to a molecule on which an enzyme that catalyzes a phosphate modification acts. The term "product" refers to the product that results from an enzyme-catalyzed phosphate modification.

The term "kinase" refers to an enzyme capapble of phosphorylating a substrate. The term "phosphatase" refers to an enzyme capable of dephosphorylating a substrate. The term "phosphodiesterase" refers to an enzyme that catalyzes the hydrolysis of the 3'-ester bond of a cyclic nucleotide (such as cAMP and cGMP) to form a noncyclized nucleotide monophosphate. The term "cyclase" refers to an enzyme that catalyzes the formation of a cyclic nucleotide (such as cAMP) and cGMP) from a nucleotide triphosphate.

The term "indium (III)" is used interchangeably with "In (III)" and "$In^{+3}$" and refers to an indium ion having unpaired electrons and a charge of +3 (plus three). Indium (III) ions can be formed in an aqueous mixture from indium salts such as indium chloride ($InCl_3$). The term "zirconium (IV)" is used interchangeably with "Zr (IV)" and "$Zr^{+4}$" and refers to a zirconium ion having unpaired electrons and a charge of +4 (plus four). Zirconium (IV) ions can be formed in an aqueous mixture from zirconium salts such as zirconium chloride ($ZrCl_4$).

The term "fluorescent" or "fluorescence" refers to the emission of electromagnetic radiation, usually visible light, caused by excitation by light or other forms of electromagnetic radiation of atoms or molecules in a substance. The term "fluorescence response" refers to one or more parameters by which the fluorescence of a fluorescent substance is characterized.

The term "fluorescence intensity" refers to the amount or intensity of light emitted from a fluorescent substance. The term "time-resolved fluorescence intensity" refers to the fluorescence intensity of a sample monitored as a function of time after excitation by a flash of light.

The term "fluorescence quenching" refers to any process which decreases the fluorescence intensity of a given substance. A variety of processes can result in quenching, such as excited state reactions, energy transfer, complex formation and colissional quenching.

The term "fluorescence resonance energy transfer" describes an energy transfer mechanism between two fluorescent molecules. A fluorescent donor is excited at its specific fluorescence excitation wavelength. By a long-range dipole-dipole coupling mechanism, this excited state is then nonradiatively transferred to a second molecule, the acceptor. The donor returns to the electronic ground state. The term "time-resolved fluorescence resonance energy transfer" is the extension of fluorescence resonance energy transfer to include a time function. The term "fluorescence polarization" refers to measurement of the polarization of fluorescent light from solutions or microscopic specimens; used to provide information concerning molecular size, shape, and conformation, molecular anisotropy, electronic energy transfer, molecular interaction, including dye and coenzyme binding, and the antigen/antibody reaction.

The present invention provides methods for assaying the activity of enzymes that catalyze phosphate modifications. Such enzymes include kinases and phosphatases which, respectively, phosphorylate and dephosphorylate, polypeptide molecules, and cyclases and phosphodiesterases which, respectively, cyclize and decyclize, nucleotide molecules. The assays provided in the present invention are useful in a variety of applications, including, without limitation, life science research, assay development, drug discovery and high-throughput screening.

The methods of the present invention are based on the specific binding by the metal ions, indium (III) ($In^{+3}$) and zirconium (IV) ($Zr^{+4}$) to a phosphate group on a phosphorylated polypeptide or to a noncyclized nucleotide. The binding is specific in that indium (III) ions and zirconium (IV) ions do not bind to unphosphorylated polypeptides or to cyclized nucleotides. The discriminate quality of these metal ions allows them to be utilized in assays that monitor the activity of enzymes that catalyze phosphate modifications since these metal ions can bind only to the substrates or to the products of the enzymatic reactions but not to both. For enzymes such as kinases and phosphodiesterase, $In^{+3}$ and $Zr^{+4}$ ions will bind to the product but not to the substrate, whereas for phosphatases and cyclases, these ions will bind to the substrate but not to the product. By measuring the extent of binding between the metal ions and the substrate or product (depending on which enzyme), the activity of the enzymes can be determined. These assays can further be used to screen for or identify substances that can modulate the activity of kinases, phosphatases, cyclases and phosphodiesterases. Finally, these assays can be applied to any kinase, phosphatase, cyclase or phosphodiesterase because the binding between the metal ions and the phosphate group can occur without regard to any specific amino acid sequence in a polypeptide or any specific base or nucleoside in a nucleotide.

The assays of the present invention are comprised of the following steps. These steps include (1) contacting the substrate with the enzyme in the presence of indium (III) ion or zirconium (IV) ion, (2) measuring a response indicative of the extent of binding between indium (III) ion or zirconium (IV) ion and either the substrate or product, and (3) correlating the response with the activity of the enzyme that affects the phosphate modification. The assays further may include contacting the substrate and the enzyme with a candidate substance such as a putative modulator before and/or during the step of contacting the substrate and enzyme with indium (III) ion or zirconium (IV) ion, and determining the ability of the candidate substance to promote or inhibit the activity of the enzyme by its effects on the extent of binding between indium (III) ion or zirconium (IV) ion and either the substrate or product.

The step of contacting assay components such as enzymes, enzyme modulators, substrates, products and indium (III) ions or zirconium (IV) ions with one another and/or with other species generally comprises any method for bringing any specified combination of these components into functional and/or reactive contact. A preferred method is by mixing and/or forming the materials in solution, although other methods, such as attaching one or more components such as the indium (III) ions or zirconium IV ions to a bead or surface, also may be used, as long as the components retain at least some function, specificity, and/or binding affinity following such attachment.

The assay components and/or sample may be supported for contact by any material capable of providing such support. Suitable substrates may include microplates, PCR plates, biochips, and hybridization chambers, among others, where features such as microplate wells and microarray (i.e., biochip) sites may comprise assay sites. Suitable microplates are described in the following U.S. patent applications, which are incorporated herein by reference: Ser. No. 08/840,553, filed Apr. 14, 1997; and Ser. No. 09/478,819, filed Jan. 5, 2000. These microplates may include 96, 384, 1536, or other numbers of wells. These microplates also may include wells having small ($\leq 50$ µL) volumes, elevated bottoms, and/or frustoconical shapes capable of matching a sensed volume.

The step of measuring a response indicative of the extent of binding generally comprises any method for effectuating such detection, including detecting and/or quantifying a change in, or an occurrence of, a suitable parameter and/or signal. The method may include fluorescence and/or nonfluorescence methods, and heterogeneous and/or homogeneous methods, among others.

Fluorescence assays involve detecting light emitted by a fluorescent compound (or fluorophore) and using properties of that light to understand properties of the compound and its environment. A typical fluorescence assay may involve (1) exposing a sample to a condition capable of inducing fluorescence from the sample, and (2) measuring a detectable fluorescence response indicative of the extent of binding between the metal ions and the substrate or product. Most fluorescence assays are based on light emitted in response to absorption of suitable excitation light. Suitable fluorescence assays include, among others, (1) fluorescence intensity, which involves measurement of the intensity of fluorescence, (2) fluorescence polarization, which involves detection of the polarization of light emitted in response to excitation by polarized light, and (3) fluorescence resonance energy transfer, which involves detection of energy transfer between a fluorescent donor and a suitable acceptor. Nonfluorescence assays involve using a detectable response other than light emitted by the sample, such as absorption, scattering, and/or radioactivity, among others. These and other fluorescence and nonfluorescence assays are described in the following materials, which are incorporated herein by reference: U.S. patent application Ser. No. 09/765,869, filed Jan. 19, 2001; and Joseph R. Lakowicz, *Principles of Fluorescence Spectroscopy* ($2^{nd}$ ed. 1999).

The detectable fluorescence response generally comprises a change in, or an occurrence of, a fluorescence signal that is detectable by direct visual observation and/or by suitable instrumentation. Typically, the detectable response is a change in a property of the fluorescence, such as a change in the intensity, polarization, energy transfer, lifetime, and/or excitation or emission wavelength distribution of the fluorescence. The detectable response may be simply detected, or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In fluorescence assays, the detectable response may be generated directly using a fluorophore associated with an assay component actually involved in binding such the substrate or indirectly using a fluorophore associated with another (e.g., reporter or indicator) component. Suitable methods and fluorophores for fluorescently labeling assay components are described in the following materials, which are incorporated herein by reference: Richard P. Haugland, *Handbook of Fluorescent Probes and Research Chemicals* ($6^{th}$ ed. 1996); U.S. patent application Ser. No. 09/813,107, filed Mar. 19, 2001; and U.S. patent application Ser. No. 09/815,932, filed Mar. 23, 2001.

Heterogeneous and homogeneous methods may be distinguished by whether they involve sample separation before detection. Heterogeneous methods generally require bulk separation of bound and unbound species. This separation may be accomplished, for example, by washing away any unbound species following capture of the bound species on a solid phase, such as a bead or microplate surface labeled with a metal ion or other suitable component. The extent of binding then can be determined directly by measuring the amount of captured bound species and/or indirectly by measuring the amount of uncaptured unbound species (if the total amount is known). Homogeneous methods, in contrast, generally do not require bulk separation but instead require a detectable response such as a fluorescence response that is affected in some way by binding or unbinding of bound and unbound species without separating the bound and unbound species.

The step of correlating generally comprises any method for correlating the extent of binding with the activity of the enzyme that affects the phosphate modification. The correlation generally may be performed by comparing the presence and/or magnitude of the response to another response (e.g., derived from a similar measurement of the same sample at a different time and/or another sample at any time) and/or a calibration standard (e.g., derived from a calibration curve, a calculation of an expected response, and/or a luminescent reference material). Thus, for example, in a polarization assay for cyclic nucleotide concentration, the cyclic nucleotide concentration in an unknown sample may be determined by matching the polarization measured for the unknown with the cyclic nucleotide concentration corresponding to that polarization in a calibration curve generated under similar conditions by measuring polarization as a function of cyclic nucleotide concentration.

EXAMPLES

The following preparations and examples are given to enable those skilled in the art to more clearly understand and to practice the present invention. They should not be considered as limiting the scope of the invention, but merely as being illustrative and representative thereof.

Example 1

Phosphodiesterase Assay Using Fluorescence Polarization

The phosphodiesterase (PDE) reaction mixture contains PDE (various concentration) and 50 nM TAMRA-cGMP in 20 ul 10 mM Tris (pH=7.2) containing 0.1% BSA. After incubation at room temperature for 1 hour, 60 ul of 10 mM $ZrCl_4$, $InCl_3$ or $GaCl_3$ in 100 mM NaAc/HAc buffer (pH=5.2) in the presence of 10 mM $ZnSO_4$ was added to the PDE reaction mixture. After one hour of incubation, the fluorescence polarization was measured using Analyst reader (Molecular Devices). The results of the experiment are shown in FIG. 1A. FIG. 1B shows a similar PDE assay in which various metallic ion salts were used. Only $ZrCl_4$, $InCl_3$ and $GaCl_3$ were able to show fluorescence signal, indicative of binding to the PDE product.

Example 2

Representation of Kinase Assay Using Fluorescence Polarization

Figure 2:
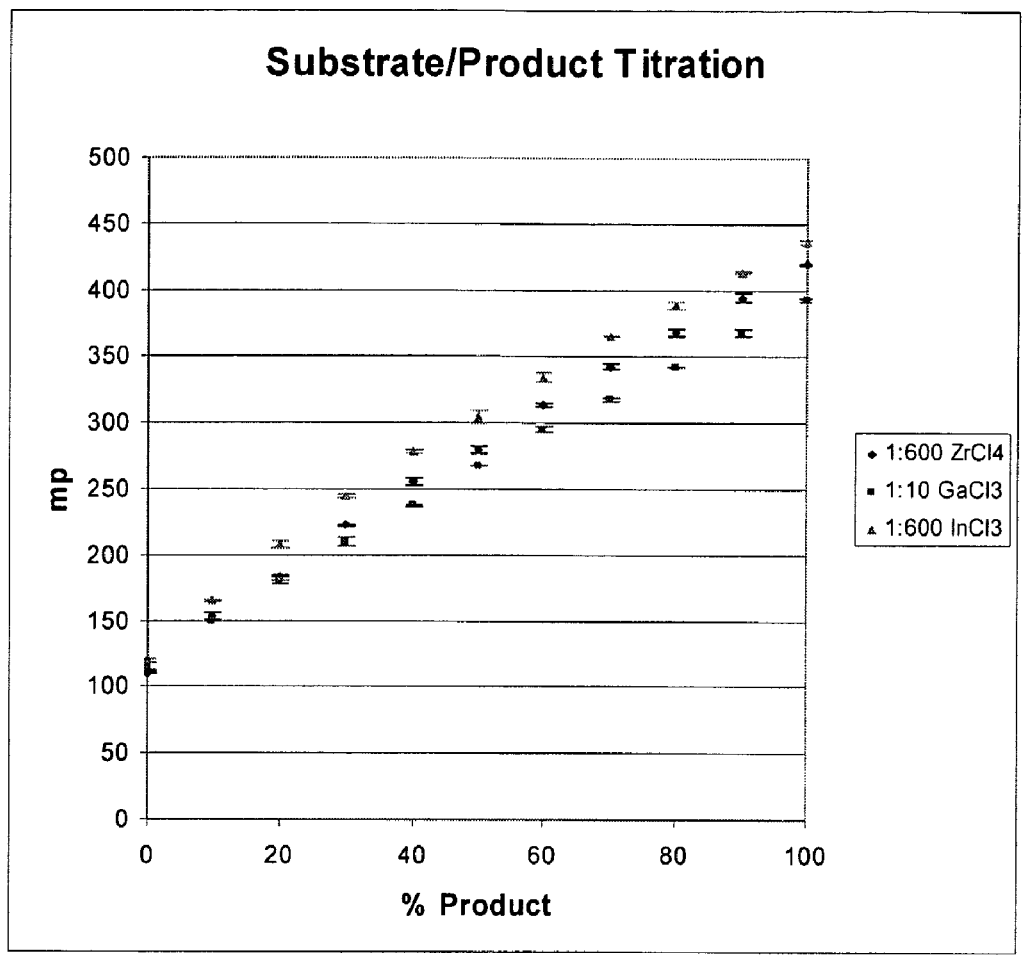
FIG. 2 shows a representation of a kinase assay with fluorescence polarization as the detection measurement using a titration of a unphosphorylated substrate and phosphorylated product.

The mixtures of TAMRA-KNSDLLTSPDVGLLK (substrate) and TAMRA-KNSDLLTS($PO_3$)PDVGLLK (product) at different ratio were used to mimic the kinase reaction mixtures. 100 mM $ZrCl_4$, $InCl_3$ or $GaCl_3$ were diluted in 100 mM of NaAc/HAc buffer (pH=5.2) containing 10 mM $ZnSO_4$. The dilution factor used for $ZrCl_4$ and $InCl_3$ was 1:600, while that used for $GaCl_3$ was 1:10. 60 ul of these salt solutions were added to the peptide mixtures. After one hour of incubation, the fluorescence polarization was measured using Analyst reader. The results of the experiment are shown in FIG. 2.

Example 3

Heterogeneous Assays

In (III) or Zr (IV) can be used to replace the Ni (II) on metal-coated plates (Pierce) or beads to separate phosphorylated molecules from nonphosphorylated molecules when phosphorylation (or de-phosphorylation) occurs. Kinase or phosphatase assay can be run using a fluorescent-labeled peptide or protein substrate. The phosphorylated peptide or protein captured to In(III) or Zr(IV) coated particles, microplates or inner surfaces of microfluidic device can be detected after washing. The washing or separation step can be omitted if a reader that can detect at single molecule or single cell level is used. Phosphodiesterase activity can be detected if a fluorophore-labeled cAMP or cGMP is used as the substrate.

Example 4

Time-Resolved Fluorescence Energy Transfer Assays

To determine the activity of kinase, phosphatase, cyclase or PDE, an acceptor (i.e. Cy5 or Fluorecein) labeled fluorescent substrate can be used. Upon the stop of the enzyme reaction, a donor (i.e. Europium complex or Terbium complex)-labeled $PO_3$-peptide (or other $PO_3$- labeled molecule) can be added together with the In (III) or Zr (IV) salt solution to the reaction mixture. The donor and acceptor pair is brought to the close proximity by In (III) or Zr (IV) when $PO_3$-metal complexes are formed, which results in fluorescence energy transfer.

Similarly, a quencher-conjugated $PO_3$-peptide (or other $PO_3$-labeled molecule), instead of the donor conjugated ones, can be used. Here the fluorescence signal change reflects the amount of un-reacted substrate for the phosphate modification enzyme reactions.

What is claimed is:

1. A method of screening for a substance that modulates the activity of an enzyme that can catalyze a phosphate modification on a substrate to form a product, said method comprising the steps of
   i) contacting the substrate and enzyme in the presence or absence of the substance and in the presence of indium (III) ion or zirconium (IV) ion, wherein the indium (III) ion or zirconium (IV) ion can bind to either the substrate or the product but not to both;
   ii) measuring the extent of binding between the indium (III) ion or ziroconiuin (IV) ion and the substrate or the product in the presence or absence of the substance; and
   iii) determining the difference in the extent of binding in step ii) between when the substance is present and when the substance is absent which correlates with the substance modulating the activity of the enzyme;
   wherein the enzyme is selected from the group consisting of kinases, phosphatases, cyclases and phosphodiesterases.

2. The method of claim 1 wherein the substrate is labelled with a fluorescent moiety, and wherein step ii) comprises measuring a detectable fluorescence response that is indicative of the extent of binding between the indium (III) ion or zirconium (IV) ion and the substrate or the product.

3. The method of claim 2 wherein the detectable fluorescence response is selected from the group consisting of fluorescence intensity, fluorescence quenching, time-resolved fluorescence intensity, fluorescence resonance energy transfer, time-resolved fluorescence resonance energy transfer and fluorescence polarization.

4. The method of claim 3 wherein the detectable fluorescence response is fluorescence polarization.

* * * * *